United States Patent [19]

Sarnoff et al.

[11] 4,226,235
[45] Oct. 7, 1980

[54] PLURAL INJECTING DEVICE

[75] Inventors: Stanley J. Sarnoff; George B. Calkins, both of Bethesda; N. Lawrence Dalling, Gaithersburg, all of Md.

[73] Assignee: Survival Technology, Inc., Bethesda, Md.

[21] Appl. No.: 6,555

[22] Filed: Jan. 25, 1979

[51] Int. Cl.³ .............................................. A61M 5/00
[52] U.S. Cl. ................................................ 128/218 F
[58] Field of Search ........... 128/218 R, 218 A, 218 F, 128/218 D, 215, 216

[56] References Cited

U.S. PATENT DOCUMENTS

| | | | |
|---|---|---|---|
| 3,552,394 | 1/1971 | Horn | 128/218 R |
| 3,572,336 | 3/1971 | Hershberg | 128/218 R |
| 3,702,608 | 11/1972 | Tibbs | 128/218 F |
| 4,031,893 | 6/1977 | Kaplan et al. | 128/218 F |
| 4,178,928 | 12/1979 | Tischlinger | 128/215 |

FOREIGN PATENT DOCUMENTS

447368 10/1912 France .................................. 128/218 F

*Primary Examiner*—John D. Yasko
*Attorney, Agent, or Firm*—Cushman, Darby & Cushman

[57] ABSTRACT

A plural injecting device comprising an outer housing assembly, a plurality of cartridge sub-assemblies, and a corresponding plurality of releasable spring sub-assemblies for effecting a forward movement of the associated hypodermic needle into the user's muscle tissue and the associated liquid medicament dosage outwardly through the needle, the sub-assemblies being mounted within the outer housing assembly so that as a result of the actuation of one of the releasable spring sub-assemblies the other releasable spring sub-assembly will be actuated so as to insure a substantially simultaneous injection of the plural dosages contained within the device. A safety arrangement in some embodiments provides for selective individual or plural dosage injection.

11 Claims, 8 Drawing Figures

PLURAL INJECTING DEVICE

This invention relates to the injection of medicaments and more particularly to improvements in injection devices of the type in which the insertion of the hypodermic needle and injection of the medicament dosage through the inserted needle are both accomplished automatically by a spring force in response to a simple actuation procedure.

It has long been recognized that there are many situations where an individual must self-inject a medicament dosage where it is not practical to provide the individual with the same syringe type of injection equipment normally utilized by professionals to inject others. It is well known that many individuals have great difficulty in performing the act of pushing a hypodermic needle into one's own flesh. To enable self injection to become a simpler, more viable procedure, so-called "automatic injectors" have been developed. Basically injectors of the automatic type provide for the storage of a medicament dosage and hypodermic needle within a housing in operative relation with a cocked or stressed spring. The stressed spring is controlled by a releasing mechanism which, when actuated, serves to release the stressed spring, thereby releasing a force sufficient to move the hypodermic needle outwardly and the medicament dosage outwardly through the needle. A safety device is provided for preventing an unwanted actuation of the spring releasing mechanism, thus insuring that actuation will take place only after a deliberate actuating procedure has been accomplished including an appropriate interengagement of the device with the muscle tissue to be injected.

Examples of automatic injectors which have been heretofore available for the injection of nerve gas antidotes and cardiac arrhythmia dosages under emergency conditions are U.S. Pat. No. 2,832,339; No. 3,712,301; and No. 3,882,863. Other examples of automatic injectors in the patented literature include U.S. Pat. Nos. 3,403,679 and 3,572,336.

U.S. Pat. No. 3,572,336 is of particular importance as background to the present invention because of the following disclosure contained therein:

"This invention can also be used to administer a plurality of drugs through a plurality of needles simultaneously. If the drugs are slightly incompatible, they can be mixed prior to injection into the patient through a single needle. In cases where the drugs are imcompatible to such a degree that they can never be combined, this invention provides means for simultaneously injecting a plurality of needles into a patient, such that different drugs may be simultaneously provided to the patient."

In support of the quoted assertion, there is shown and described a specific embodiment suitable for slightly incompatible drugs and a different specific embodiment suitable for fully incompatible drugs. In both instances, however, the plural capability is obtained by simply forming a single dose-receiving member with a plurality of parallel dose-receiving chambers rather than a single chamber and directing the dosages either to a common needle or separate needles. In both instances, the discharge of the plural dosages is simultaneously accomplished by a single plunger moved through a dosage discharging stroke by a single spring. Moreover, actuation of the single spring is made to take place as the final part of a two spring sequential movement, the first part of which commences as a result of a single actuation of a single actuating mechanism and functions to initially move the needle or needles into the user.

While there is thus contemplated in the prior art two specific situations where plural dosages within a single device are desirable, the present invention contemplates other specific situations where the specific prior art embodiments would not be appropriate.

Such a situation is presented in the case of nerve gas antidote dosages embodying a combination of ingredients. A combination of ingredients as presently utilized is provided to get the combined effects of a plurality of ingredients, the individual effects of each of which are known. In some cases an individual ingredient is utilized for a given beneficial effect despite known disadvantageous effects thereof because other ingredients capable of achieving the same beneficial effect without such disadvantageous effects are not yet known. It is of extreme importance to simplify the implementation of any newly developed replacement ingredient and it is the object of the present invention to provide for the accomplishment of such simplified implementation.

In accordance with the principles of the present invention, this objective is obtained by utilizing within a common outer housing assembly a plurality of separate hypodermic needles, a corresponding plurality of separate dosage containers, a corresponding plurality of separate stressed springs, and a corresponding plurality of separate releasing mechanisms. Safety means is provided to control the plurality of releasing mechanisms and actuating means is provided to insure actuation of at least one of the releasing mechanisms. Of critical significance is the provision of means mounting the components within the outer housing assembly so as to insure that as a result of the actuating of the releasing mechanism actuated by the actuating means the other releasing mechanism or mechanisms will be actuated.

With this arrangement, the present invention provides a plural dosage device in which one of the plural ingredient dosages can be quite simply bodily replaced in the event that a new and better ingredient is developed. Since each dosage is provided with its own driving spring and releasing mechanism, the remaining dosages will be left with properly sized springs and properly sized releasing mechanisms and additional springs and releasing mechanisms can be properly sized for the new ingredients. Again, it is important to note that mounting means for the components is provided for insuring that when one releasing mechanism is actuated whatever other releasing mechanisms are present will also be actuated as a result of the first actuation.

The provision of a mounting means to insure generally simultaneous actuation of all releasing mechanisms is important since it has been found that reliable simultaneous actuation cannot be reliably achieved simply by the provision of plural actuating mechanisms or by providing a single actuating mechanism to actuate plural releasing mechanisms. In known systems actuation is accomplished by a manual movement of a structure through an actuating stroke which movement is transmitted to the releasing mechanism which, in turn, must be moved through a releasing stroke during the manually effected actuating stroke of the actuating structure. Moreover, in known arrangement both the actuating stroke of the actuating structure and the releasing stroke of the releasing mechanism must take place against a spring force. Thus plural actuation by a single actuating movement would require exact correlation of plural releasing strokes and plural spring forces resisting the same, whereas plural actuation by plural actuating movements would require exact correlation of the plural actuating strokes and plural spring forces resisting the same. Such exactitude cannot be provided with any great reliability. In accordance with the principles of the present invention, such reliability is achieved by providing a mounting means which will insure generally simultaneous plural actuation as a result of a single actuation without the necessity of relying upon either the initial manual actuating movement itself or subsequent manual actuating movements.

In one embodiment of the invention, the mounting means operates on a principle of inertia. In other embodiments the mounting means operates on a principle of transmitting the motion of a part of the releasing mechanism of the initially actuated releasing mechanism to effect the releasing stroke of the other releasing mechanism. Still another embodiment operates on the principle of sensing the movement of a tubular support for the initial dosage container and needle resulting from the initial actuation to release a separate spring actuating mechanism for effecting the actuation of the second releasing mechanism.

It is of importance that in several of these embodiments it is possible to provide for the selective actuation of any one or all of the plural dosages provided simply by retaining the safety in operative position with respect to the dosages which are not to be discharged. Thus, with the present invention it is, by the simple expedient of either providing separate safeties for each of the releasing mechanisms or a single safety which cooperates with all of the releasing mechanisms, possible to achieve either selective single discharge or simultaneous plural discharge. Such capability as previously indicated is of particular significance in connection with the provision of automatic devices useful in injecting antidotes for nerve gases. In the case of known single dosage devices, as for example, devices of the type described in U.S. Pat. No. 3,882,863, three chemical additives or ingredients are presently utilized together, namely, Atropine, Benactazine and TMB4, which is an oxime. Each of these ingredients exerts different mode of protection with regard to the toxification with nerve gases. Of these ingredients, for example, Benactazine is a psycho-active drug and a significant percentage of individuals, when self-injecting an antidote containing this ingredient, will have halucinatory and psycho-genetic aberrations of major proportions. By maintaining the Benactazine in a separate container within the outer housing of a plural dosage device in association with its own hypodermic needle, its own stressed spring, its own releasing mechanism and its own safety, it becomes readily possible to retrofit such a unit in the event that a more effective ingredient should be subsequently developed. Moreover, by providing this capability it may be desirable in some situations to withhold the Benactazine while shooting the other drugs, which can be readily accomplished simply by leaving in the safety for the Benactazine.

Other advantages accruing as a result of this provision include the advantage of improvement in stability characteristics. For example, one factor which importantly influences the stability of a compound is the pH or hydrogen ion concentration at which it is maintained. Atropine is very stable at a pH of 4.2, while at a pH of 6 or 7 it will fall apart very rapidly. Another important factor relating to the stability of the compound is the rubber to which it is exposed, if any, in its container. Consequently, with the present arrangement any new ingredient which would be developed would not have to be made compatible with the other ingredients in terms of its pH stability or its rubber compatibility. Moreover, it would not require the same solvent.

While the present invention has particular advantages in connection with devices used to contain chemical warfare antidotes, the invention has general applicability and makes it possible to store a plurality of drugs in a separate environment which is most compatible with their individual shelf lives. Moreover, the invention enables the selection of the most advantageous concentration for the drug, that is, the volume in which the drug is dissolved which is known to favor its stability and influences the rate of absorption after injection into the body. In regard to the absorption rate, it is known that one can, in general, increase the rate of absorption by using a lower volume for any given amount of drug injected. This has been demonstrated to be the case in many instances. Thus, by following the principles of the present invention, it becomes possible to make plural injections of the same drug instead of one, and having, therefore, a smaller volume of injectate at each injection site which can demonstrably favorably influence the rate of absorption.

A further advantage is that by the use of a plural dosage device which simultaneously makes plural injections, a larger volume of any given injectate can be given without causing discomfort and also creating a situation in the tissues that would favor rapid absorption. That is, one can comfortably anticipate that if two injections of 3 ml each were made in different sites, the rate of absorption of the injected drug would be more rapid than if the drug in an amount of 6 ml were injected into a single site. In addition, two injections of 3 ml of a given drug in different sites will produce less pain and discomfort to the patient than 6 ml injected into a single site. A further consideration is that when one injects large volumes, pressure is built up in the tissue as a result of the injection of higher volumes, which tends to promote loss of the injectate from the tissues through the needle track. Here again, by using two different injection sites of 3 ml each, by way of example, pressure build-up at these two separate sites will be less than that pressure build-up created by a single injection of 6 ml in one site.

These considerations become important in the case of drugs known to exist and to have a desirable therapeutic objective in which (1) the solubility constraints imposed by the nature of the drug is such that a large volume must be used or (2) by virtue of the amount of drug that needs to be injected, the concentration of the drug will produce tissue irritation and, therefore, be unacceptable if given in a small volume.

It will be understood that the above considerations are feasible only so long as it can be assured that the plural dosages will be injected simultaneously. In dealing with a plural dosage device, each dosage of which is provided with its own separate hypodermic needle, it will be understood that if activation of only one of the releasing mechanisms takes place and only one of the needles goes into the tissue and only one of the dosages is injected, the user will have the impression that the injector has functioned for its intended use and withdraw it. The individual will then see that there is a needle sticking out and is unlikely to push that needle back into the flesh so as to position the device in an attitude suitable to accomplish the injection of the other dosage. As previously indicated, generally simultaneous injection is insured in accordance with the principles of the present invention by providing mounting means for the components which insure that the other releasing mechanism or other releasing mechanisms provided are actuated as a result of the actuation of the initial releasing mechanism.

It is a further object of the present invention to provide a device of the type described which is simple but effective in operation and economical to manufacture.

These and other objects of the present invention will become more apparent during the course of the following detailed description and appended claims.

The invention may best be understood with reference to the accompanying drawings, wherein an illustrative embodiment is shown.

In the drawings.

Figures 1, 2:
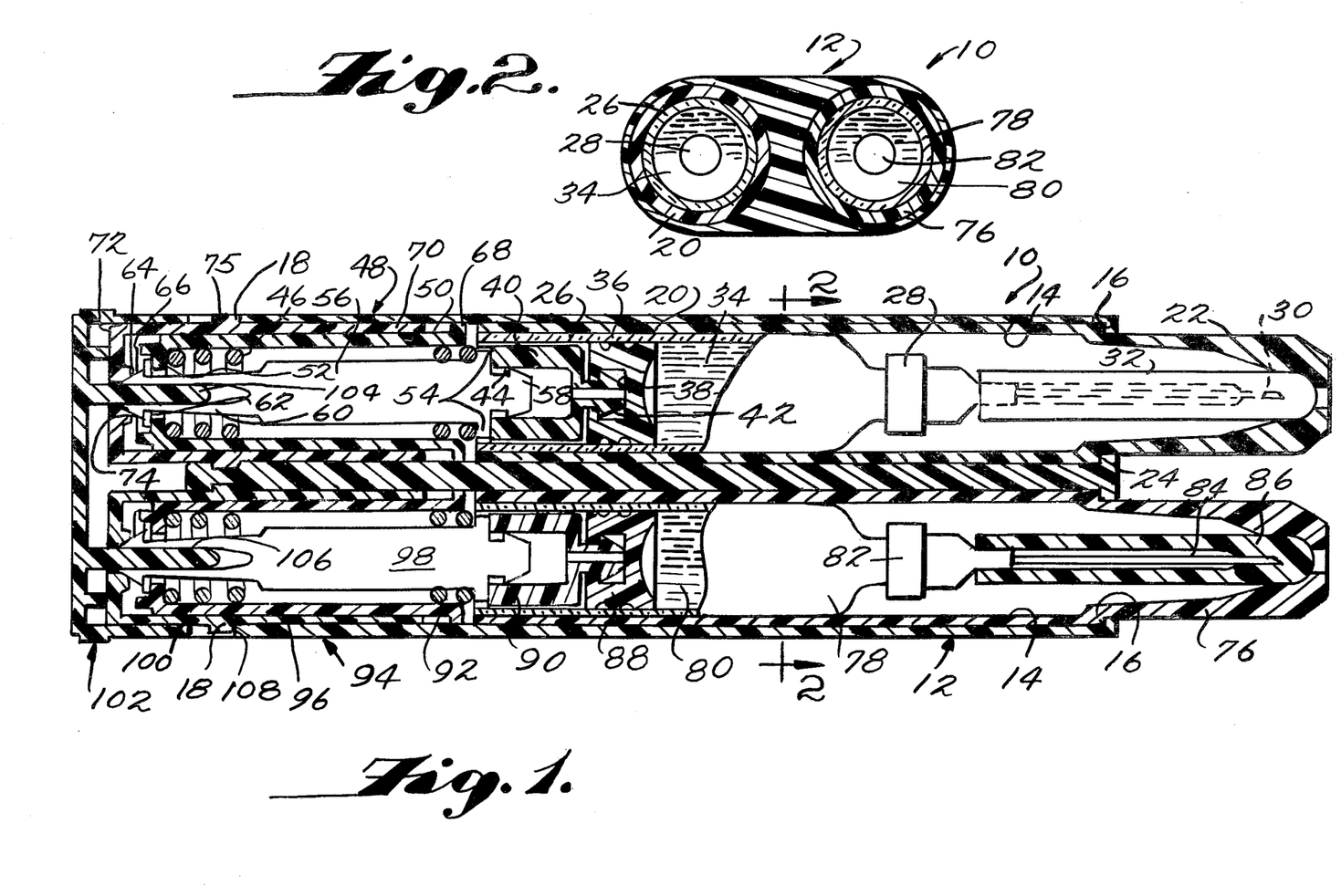
FIG. 1 is a longitudinal sectional view of one embodiment of a plural injector device embodying the principles of the present invention.
FIG. 2 is a sectional view taken along the line 2—2 of FIG. 1.

Referring now more particularly to the drawings, there is shown in FIGS. 1 and 2 thereof one form of a plural dosage injecting device embodying the principles of the present invention which is generally indicated by the reference numeral 10. The plural dosage injecting device 10 includes an outer housing 12 which, as shown, is in the form of a one-piece plastic molding defining a pair of side-by-side cylindrical chambers 14. One end of each of the chambers 14 is open and the other end is partially closed, as by an annular flange 16. Formed within the opposite end portion of each of the chambers 14 is an annular groove 18 which serves a purpose hereinafter to be more fully explained. Mounted within a first one of the cylindrical chambers 14 is a first container support 20 in the form of a tubular member having the major portion thereof formed with a cylindrical exterior periphery slidably fitting within the end portion of the chamber 14 adjacent the flange 16. The tubular member 20 includes a forwardly extending nose portion 22 of an exterior cylindrical configuration sufficient to extend through the flange 16. The exterior transition between the nose portion 22 and the remainder of the tubular member 20 provides an annular shoulder 24 which is adapted to normally engage the associated annular flange 16. Slidbly mounted within the tubular member 20 is a first glass ampule or dosage container 26. Preferably, the container is formed of glass, generally in the form of a necked bottomless bottle. Fixed to the necked end of the container 26 is a cap assembly 28 carrying a longitudinally forwardly extending hypodermic needle. The exterior of the hypodermic needle 30 is covered by a shock absorbing resilient sheath 32 in accordance with the teachings contained in Sarnoff et al. U.S. Pat. No. 3,882,863, the disclosure of which is hereby incorporated by reference into the present specification. The cap assembly 28 provides an interior resilient diaphragm (not shown) constructed in accordance with the teachings contained in Sarnoff et al. U.S. Pat. No. 3,391,695, the disclosure of which is hereby incorporated by reference into the present specification. The diaphragm serves to seal the metallic material which forms the hypodermic needle 30 from the interior of the container 26 which has therein an appropriate liquid medicament dosage, indicated by the numeral 34. The end of the container opposite from the cap assembly 28 is closed by a plunger member 36 which, as shown, is in the form of a piston of resilient material formed to provide an interior rearwardly facing socket 38.

In the embodiment shown, the medicament dosage 34 is of a volume somewhat less than the total capacity of the container 26 and consequently plunger 36 is shown disposed in spaced relation within the opposite end of the container 26. A spacer member 40 is mounted in the end of the container and has a pronged forward portion 42 engaged within the socket 38 and a socket portion 44 formed in the rear portion thereof. The spacer member 40 thus forms a part of the plunger means which serves to move the liquid medicament 34 outwardly through the hypodermic needle after the diaphragm has been ruptured through hydraulic pressure. It will be understood that the dosage amount can be varied by varying the longitudinal size of the spacer member 40 or by eliminating the spacer member entirely when a maximum volume dosage is desired.

For purposes of effecting the outward movement of the dosage there is provided a power pack sub-assembly which includes a first coil spring 46 retained in stressed condition by a first releasing mechanism, generally indicated at 48. The releasing mechanism includes an inner tube or sleeve 50 having an interior cylindrical periphery of a size sufficient to receive the spring 46 therein. At one end of the sleeve 50 is a radially inwardly extending flange 52 which serves to abuttingly receive one end of the stressed spring 46. The opposite end of the stressed spring 46 extends outwardly from the opposite end of the inner tube or sleeve 50 and is engaged by a pair of outwardly extending tabs 54 formed on one end portion of an elongated member 56 in the form of a metallic plate. The end of the elongated member 56 adjacent the tabs 54 is formed with a tongue 58 of a size to engage within the socket 44 in the end of spacer 40. The elongated member extends rearwardly from the tabs 54 through the interior of the spring 46 and has formed on the opposite rearward end thereof a pair of spring fingers 60 having forwardly facing locking shoulders 62 formed on the exterior thereof and rearwardly and inwardly inclined cam releasing surfaces 64 on the rearward extremities thereof. The locking shoulders 62 are adapted to engage a suitable locking disk 66 engaged with the rearward surface of the flange 52 of the inner tube.

The forward end of the inner tube 50 is formed with a radially outwardly extending annular flange 68 which is spaced from the forward end of an outer tube 70 forming a part of the releasing mechanism 48. The outer tube 70 is slidably mounted over the exterior periphery of the inner tube and has at its rearward end a centrally apertured end wall 72 having forwardly and outwardly inclined cam surfaces 74 formed on the central portion thereof, disposed in engagement with the inclined cam surfaces 64 on the spring fingers 60. As shown, the exterior periphery of the outer tube 70 is formed with an annular projection or ridge 75 adapted to engage within the associated annular groove 18 formed in the associated chamber 14. The container support member 20, container 26, cap 28, needle 30, sheath 32, plunger 36 and spacer 40 constitute a first dosage cartridge sub-assembly and the spring 46, inner tube 50, elongated member 56, outer tube 70 and locking disk 66 constitute a first power pack sub-assembly for operating the cartridge sub-assembly.

The plural dosage injecting device 10 includes a second cartridge sub-assembly similar to the first which includes a second container support member 76, a second container 78, second dosage 80, second cap 82, second needle 84, second sheath 86, second plunger 88 and second spacer 90; and second power pack sub-assembly similar to the first including second spring 92, second releasing mechanism 94, second inner tube 96, second elongated member 98, second locking disk and second outer tube 100.

The plural injecting device 10, as shown, includes a safety mechanism which, as shown, is in the form of a single molded safety cap 102 which fits over the rearwardly protruding ends of both the first outer tube 70 and the second outer tube 100. The safety cap member 102 includes a first safety plug 104 which in its operative position extends between the first spring finger 60 of the first elongated member 56 to prevent inward movement thereof and a second safety plug 106 which cooperates in a similar fashion with the spring fingers of the second elongated member 98.

It is important to note that the plural injecting device 10 provides means for mounting the second cartridge sub-assembly and second power pack sub-assembly within the outer housing 12 so that as a result of the actuation of the releasing mechanism 48 of the first power pack to effect injection of the first dosage 37, the second releasing mechanism 94 will be actuated to generally simultaneously inject the second dosage 80. This mounting means in the case of the plural injecting device 10 includes the simple sliding reception of the second container support member 76 within the second chamber 14 and the fixed engagement of the second outer tube 100 within the outer end of the second chamber 14 as by engagement of a second annular ridge 108 within the associated annular groove 18.

The second container support member 76 is thus mounted within the outer housing 12 in a manner substantially identical with the mounting of the first container support member 20 and the mounting of the second outer tube 100 within the outer housing is substantially identical with the mounting of the first outer tube 70 within the outer housing. Consequently, the plural injecting device 10 has the characteristic that not only will the second dosage be substantially simultaneously injected as a result of the injection of the first, but the reverse operation is likewise insured, namely, the first dosage 34 will be substantially simultaneously injected as a result of the injection of the second dosage 80 in the event that the second releasing mechanism 94 is initially actuated, rather than the first releasing mechanism 48. The operation of the plural injecting device 10 will be described in relation to an operation in which the first releasing mechanism 48 is actuated initially, it being understood that the device will function in a reverse manner when the second releasing mechanism 94 is the first to be actuated.

When the user desires to use the multiple injecting device 10, the user first removes safety cap 102. The user then manually grips the exterior of the outer housing 12 and positions the nose pieces of the first and second container support members 20 and 72 into engegement with the area where the injection is to be made as, for example, the thigh. The user then applies an inward movement to the outer housing 12 which has the effect of relatively moving the first and second cartridge sub-assemblies together with the first and second elongated members 56 and 98 respectively rearwardly within their chambers 14 within the outer housing 12 by virtue of the engagement of the outer housings with their respective outer tubes. The rearward movement of the first elongated member 56 with respect to the first outer tube 70, which is held stationary within the outer housing 12 by virtue of the engagement of its annular ridge 74 within the annular groove 18, causes the cam surfaces 64 on the spring fingers 60 of the elongated member 56 to move along cam surfaces 74 resulting in an inward movement of the spring fingers toward one another which has the effect of disengaging the locking shoulders 62 thereof from their locking disks 66.

The nose portion 22 of the first container support member 20 serves as the actuating means of the first cartridge sub-assembly, the actuating stroke thereof constituting the amount of rearward movement of the member 20 within the chamber 14 required to effect disengagement of the locking shoulders 62 with the locking disk 66 as aforesaid. Moreover, the inward movement of the spring fingers 60 during which this disengagement takes place constitutes the releasing stroke of the releasing mechanism 48. When this release or disengagement takes place, the stressed condition of the spring 46 is released which has the effect of moving rearwardly the first inner tube 50 and of moving forwardly the first elongated member 56 which, in turn, effects a forward movement of the entire first cartridge sub-assembly. The rearward movement of the relatively small mass represented by the inner tube 50 is stopped by engagement with the end wall 72 of the outer tube 70. The forward movement of the relatively large mass represented by the first elongated member 56 and all of the components which make up the first cartridge sub-assembly is first resisted by the interengagement of the shoulder 24 of the container support member 20 with the flange 16 of the outer housing. As this relatively large mass meets this resistance, the inertia thereof will impart a forward movement or impact to the outer housing 12. However, since the second cartridge sub-assembly is not rigidly fixed to the outer housing member 12, but is mounted therein for relative rearward movement against the action of the second spring 92, the mass represented by the second cartridge sub-assembly and the second elongated member 98 tends by inertia to remain stationary during the forward impact movement of the outer housing 12. Thus, there is accomplished by virtue of the manner in which the components are mounted within the outer housing 12, a relative forward movement of the outer housing with respect to the second cartridge sub-assembly and second elongated member 98 as a result of the release of the first releasing mechanism 48 which will have the effect of actuating the second releasing mechanism 94. The actuation of the second actuating mechanism 94 through the inertia action achieved as a result of the actuation of the first releasing mechanism occurs substantially simultaneously with the latter or immediately thereafter. This is particularly true since some relative rearward movement of the second cartridge sub-assembly and second elongated member 98 with respect to the outer housing will have already taken place by virtue of the actuating movements already accomplished to achieve movement of the first actuating means through its actuating stroke. It will also be understood that in addition to the inertial effects resulting from the forward movement of the first cartridge sub-assembly under the action of the released spring 46, the forward movement of the first needle 30, the first cap 28, the first container 26, the first dosage 34, the first plunger 36 and the first spacer 40 will continue after the forward movement of the first support member 20 has been stopped until needle 30 reaches a fully extended position within the user's muscle tissue. After this position is reached, which is determined by the compression of the shock absorbing sleeve 32, the forward movement of the plunger 36 and spacer 40 will continue under the action of the spring 46 which has the effect of initially bursting the diaphragm seal and then moving the dosage 40 through the needle 30 into the muscle tissue of the user. Forward movement is arrested when plunger 36 reaches the full extent of its movement within the container 26.

It will be understood that the second dosage 80 is injected in a similar manner by the forward movement of the second elongated member 98 under the action of the second spring 92 after the forward movement of the second container support member 76 has been arrested and the second needle 84 has been moved to its extended position.

It is within the contemplation of the present application to make the safety means 102 into two separate cap pieces, one of which contains the first safety plug 104 and the other of which contains the second safety plug 106. Where two separate cap pieces are provided, the user will have the option of achieving the aforesaid generally simultaneous injection of both dosages by removing both cap pieces, or of injecting only one of the dosages by removing only the safety cap piece associated with that dosage.

Figure 3:
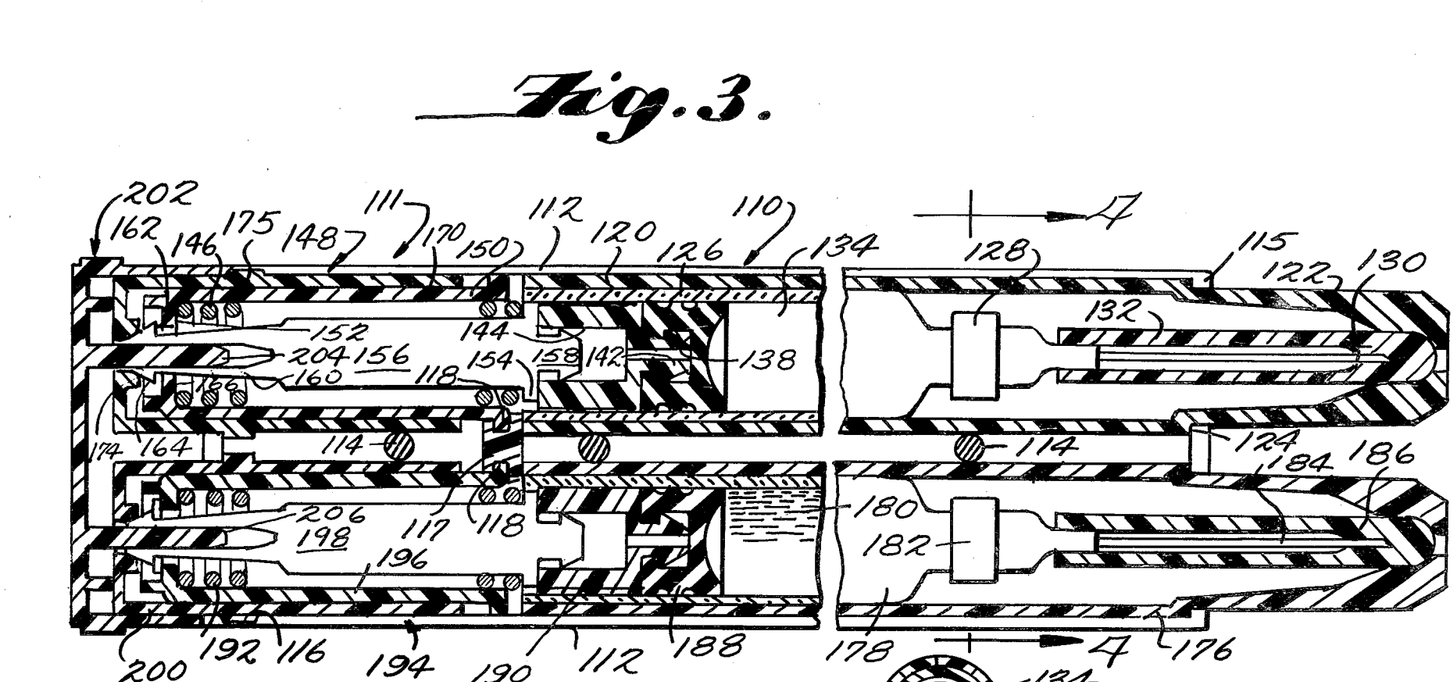
FIG. 3 is a longitudinal sectional view similar to FIG. 1 of another embodiment of the present invention.
Figure 4:
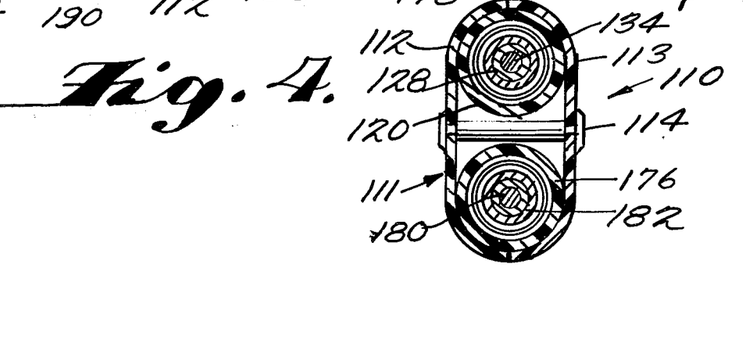
FIG. 4 is a cross-sectional view taken along the line 4—4 of FIG. 1.

Referring now more particularly to FIGS. 3 and 4, there is shown therein another form of a plural dosage injecting device embodying the principles of the present invention which is designated by the reference numeral 110. The device 110 includes an outer housing assembly 111 in the form of two separate outer housing halves 112 and 113 molded of a suitable moldable material, such as plastic. The housing halves, when disposed together, provide a chamber suitable to receive therein first and second cartridge sub-assemblies and respective first and second power pack sub-assemblies, each of which is constructed in a manner similar to the first cartridge sub-assembly and first power pack sub-assembly described in detail above. The two housing halves 112 and 113 are arranged to be rigidly secured together in operative relation with respect to the sub-assemblies as aforesaid by a plurality of spacer rivets 114 which serve not only to rigidly secure the two housing halves together in operative relation but to retain the first and second sub-assemblies within the outer housing assembly in operative spaced relation.

Rather than to repeat the description of the components which are contained within each of the subassemblies, since the sub-assemblies are substantially identical to those already described, comparable components have been provided with corresponding reference numerals preceded by the numeral 1, or by changing the reference numerals 100, etc. to 200, etc.

The mounting means of the plural injecting device 110 which serves to accomplish the actuation of the second releasing mechanism 194 as a result of the actuation of the first releasing mechanism 148 includes the provision of peripheral inwardly turned flanges 115 on the forward ends of the housing halves 112 and 113 which function in a manner similar to the flanges 16 previously described and peripheral grooves 116 in the rearward interior of the housing halves 112 and 113 which function in a manner similar to the grooves 18 previously described. In addition, the mounting means includes a sliding block 117 which is mounted within the central rearward portion of the outer housing assembly 111 for longitudinal sliding movement between the housing halves 112 and 113. The block includes a pair of oppositely outwardly facing grooves 118, a first one of which is adapted to receive therein the adjacent portion of the annular flange 168 on the first inner tube 150. The other groove 118 receives therein the adjacent portion of the annular flange on the second inner tube 196.

It will be noted that the plural injecting device 110 also includes a safety cap assembly 202 which is similar to the safety cap 102 previously described.

The plural injecting device 110 will operate in the same fashion as the plural injecting device 10. However, in addition it will be noted that the slide block 117 serves to mechanically interconnect the first inner tube 150 with the second inner tube 196 so that the rearward movement of the first inner tube 150 occasioned as a result of the actuation of the first releasing mechanism 48 will be mechanically transmitted to the second inner tube 196, thus mechanically providing sufficient relative movement between the second inner tube 196 and the second outer tube 200 to insure movement of the second releasing mechanism through a releasing stroke greater than the releasing stroke of the first releasing mechanism. Stated differently, the operation is such that first inner tube 150 will have an initial rearward movement as the first releasing mechanism moves through its releasing stroke and a final shorter rearward movement as the first spring is released, both of which are transmitted to the second outer tube to positively insure sufficient rearward movement thereof to accomplish its releasing stroke even though the length of its releasing stroke exceeds slightly the length of the releasing stroke of the first inner tube.

Figures 5, 6:
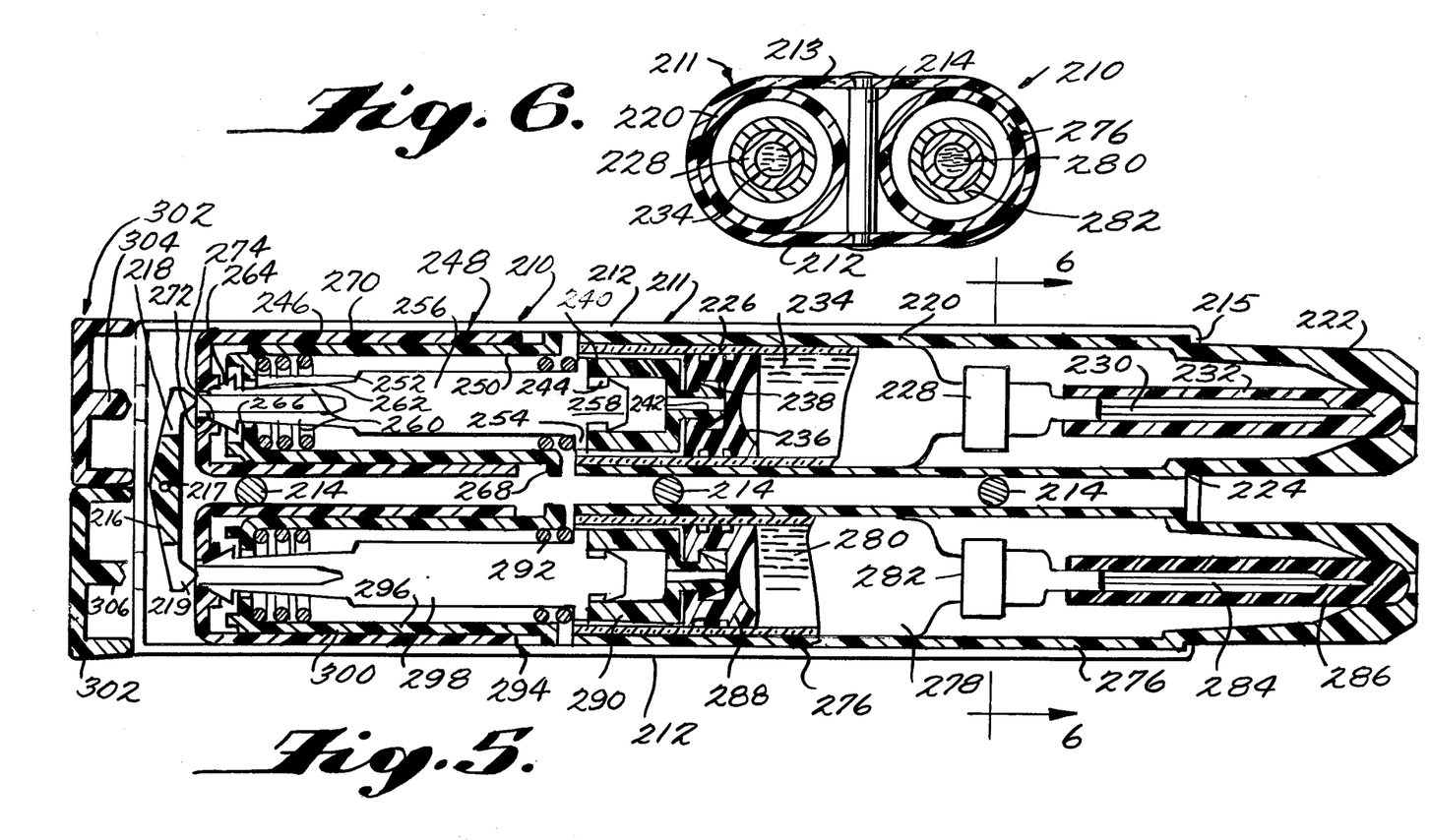
FIG. 5 is still another view similar to FIG. 1 showing still another embodiment of the present invention.
FIG. 6 is a sectional view taken along the line 6—6 of FIG. 5.

Referring now more particularly to FIGS. 5 and 6 of the drawings, there is shown therein still another form of a plural injecting device embodying the principles of the present invention which is generally designated by the reference numeral 210. The plural injecting device 210 is similar to the plural injecting devices 10 and 110 previously described, in that it includes first and second cartridge sub-assemblies operated by first and second power pack sub-assemblies, each cooperating pair of sub-assemblies being constructed similar to the pair of cooperating sub-assemblies described in detail in connection with the plural injecting device 10. Here again, rather than to repeat the detailed description of these sub-assemblies, the various parts have been designated by reference numerals corresponding to those previously utilized except that a prefix 2 has been added or, alternatively, where three digit numerals are used, the first digit has been changed to 3.

The plural injecting device 210 includes an outer housing assembly 211 which is similar to the outer housing assembly 111 previously described, in that it is made up of two cooperative halves 212 and 213 held together by appropriate suitable fastening means, such as rivets 214. The forward end of the outer housing halves 212 and 213 includes inwardly directed peripheral flanges 215 which are constructed similar to the flanges 115 and perform similar functions. The plural injecting device 210 differs from the plural injecting device 110 in that, rather than providing peripheral grooves 116, the housing halves are extended rearwardly to receive therein a lever 216. Lever 216 has its central portion pivoted to the outer housing assembly 211 by a pivot pin 217 extending between the housing halves 212 and 213. The outer ends of the lever 216 are bifurcated, as indicated at 218 and 219, so as to receive therebetween safety plugs 304 and 306 respectively forming a part of separate safety caps 302 and 302'.

The operation of the plural injecting device 210 is similar to the plural injection device 10 in that the mounting means for the two pairs of sub-assemblies is such that whichever one of the cooperating pairs of sub-assemblies is initially actuated, the mounting means will be operable to insure that as a result of such actuation the releasing mechanism of the other pair of cooperating sub-assemblies will be actuated. Moreover, the arrangement is capable of selective operation and it is for this reason that separate cap members are illustrated, although again it will be understood that a single safety cap such as the safety cap 102 may be provided if desired.

The operation of the plural injecting device 210 will be described in relation to a user manipulation in which the first releasing means 248 is initially actuated. Of course, prior to actuation, safety caps 302 and 302' are first removed. As before, initial actuation is accomplished by the user manually gripping the exterior of the outer housing 211 and moving the same toward the muscle area where injection is to take place. During this movement nose piece 222 of the first container support member 220 will engage the skin of the user together with the nose piece of the second support member 276. In terms of relative movement, the first and second catridge sub-assemblies are thus moved rearwardly within the housing assembly 211 carrying therewith first and second elongated members 256 and 298. However, relative rearward movement of the first outer tube 270 and second outer tube 300 with respect to the outer housing is resisted by virtue of the engagement of the bifurcated ends 218 and 219 of the lever 216 therewith. The relative movement which thus occurs between the first elongated member 256 and first outer tube 270 causes cam surfaces 264 to move relative to the cam surfaces 274, thereby moving spring fingers 260 inwardly toward one another until locking shoulders 262 move out of engagement with the locking ring 266. The releasing mechanism 248 is thus actuated, releasing the first stressed spring 246 which initially causes the inner tube 250 to move rearwardly until the rear end thereof engages the end 272 of the outer tube 270. In this way, the initial movement imparted by the release of the first stressed spring 246 results in a rearward movement of the first outer tube 270, which rearward movement is imparted to the lever 216 which acts, in turn, to impart a forward movement to the second outer tube 300. This additional relative movement imparted to the second outer tube 300 is sufficient to insure the movement of the second releasing mechanism 294 through its actuating stroke. The manner in which injection takes place following actuation is the same as previously described.

It will be noted that when either one of the safety caps 302 or 302' is removed with the other being retained in its operative position, the presence of the corresponding safety plug in its operative position between the spring fingers of the associated elongated member effectively rigidifies the corresponding power pack sub-assembly with the associated cartridge sub-assembly. Under these circumstances lever 216 serves to fixedly retain the associated outer tube against rearward movement, thereby insuring actuating movement of the releasing mechanism associated with the power pack sub-assembly having its safety cap removed.

Figures 7, 8:
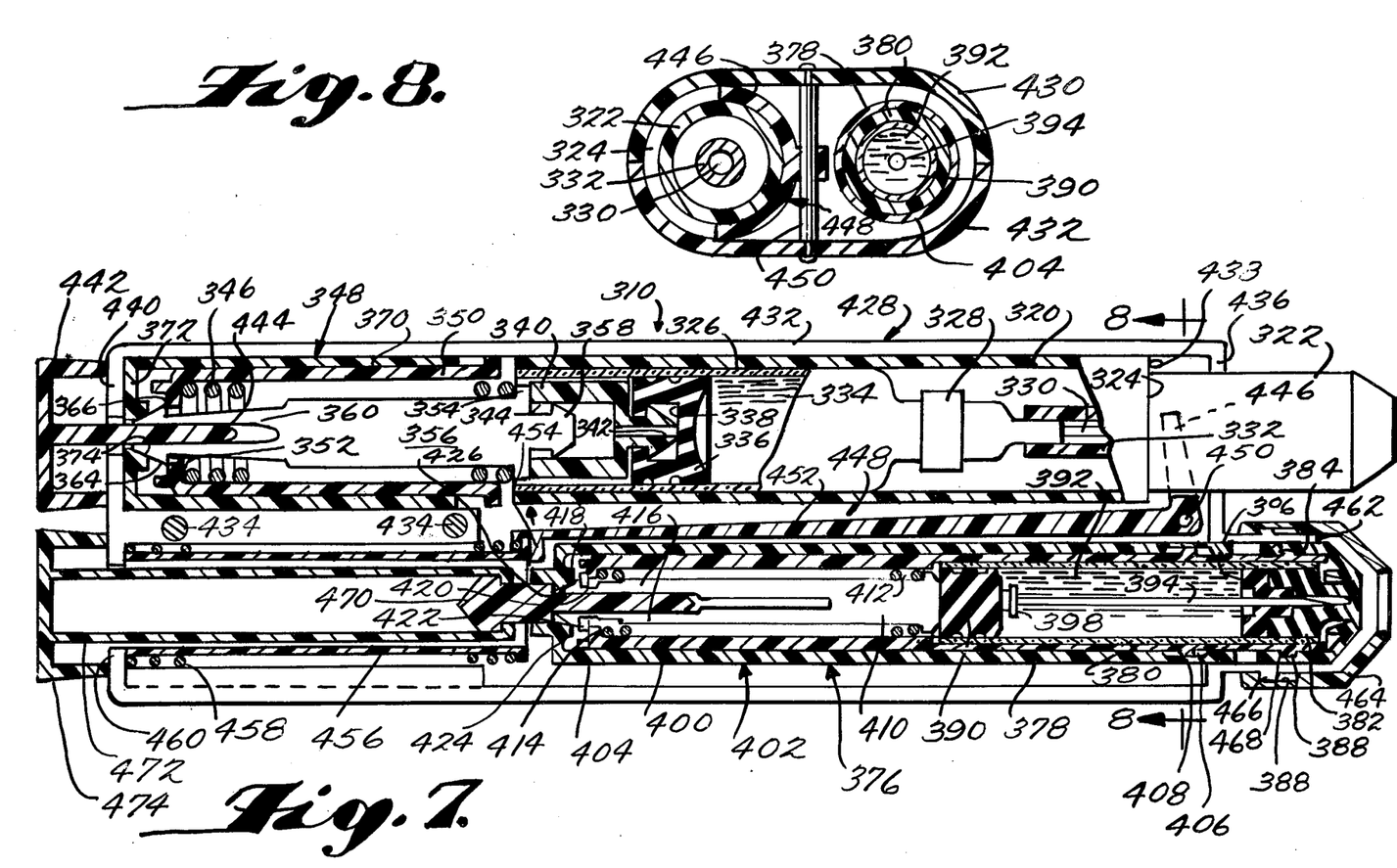
FIG. 7 is still a further view similar to FIG. 1 showing still another embodiment of the present invention.
FIG. 8 is a cross-sectional view taken along the line 8—8 of FIG. 7.

Referring now more particularly to FIGS. 7 and 8, there is shown therein still another form of a plural injecting device embodying the principles of the present invention which is generally indicated by the numeral 310. The plural injecting device 310 is similar to the plural injecting devices 10, 110 and 210 previously described to the extent that it includes a first cartridge sub-assembly and cooperating first power pack sub-assembly constructed in the manner described above in detail in connection with the plural injecting device 10. The plural injecting device 310 includes a second automatic injecting unit or assembly, generally indicated at 376, which is constructed in accordance with the teachings contained in Sarnoff U.S. Pat. No. 2,832,339, the disclosure of which is hereby incorporated by reference into the present specification.

As shown, the unit 376 includes a tubular dosage container support member 378, the forward portion of which is formed with a counterbore for receiving therein a cylindrical dosage container 380. The forward end of the container is closed by a stopper or plug 382 of suitable rubber or plastic material. Plug 382 is retained in closing relation with the forward end of the container 380 by an end cap member 384 of molded plastic material. The cap is retained on the container support member 378 by interengagement of an annular ridge 386 formed on the exterior periphery of the tubular member 378 with an annular groove 388 formed on the interior periphery of the cap member 384.

The rearward end of the dosage container 380 is closed by a plunger 390 which is slidably sealingly engaged within the rearward end thereof so as to enclose within the container a dosage 392 of a liquid medicament. A hypodermic needle 394 is disposed within the container 380 and has its pointed end disposed within a recess formed in the plug 382. A disk 396 of plastic is disposed within the forward end of the container 380 in surrounding sealed relation with the hypodermic needle 394 and in abutting engagement with the plug 382. The disk serves to releasably hold the needle in its storage position and to provide peripheral sealing therefor during the dosage injecting stroke of the plunger 390. The opposite end of the hypodermic needle 394 is enlarged as indicated at 398, for engagement by the plunger and provides radially extending grooves for communicating the dosage 392 with the hollow interior of the hypodermic needle 394 when the plunger 390 is in engagement therewith.

The rearward end portion of the container support member 378 constitutes an inner tube portion 400 which forms a part of a releasing mechanism, generally indicated at 402, similar to the releasing mechanisms previously described. The releasing mechanism 402 also includes an outer tube 404 which is slidably mounted over the inner tube portion 400 for limited reciprocating movement as determined by an annular ridge 406 formed on the exterior periphery of the tubular container support member 378 at a position spaced rearwardly from the annular ridge 386. The annular ridge 406 is adapted to engage within an elongated annular groove 408 formed on the interior periphery of the outer tube 404.

The releasing mechanism also includes an elongated member 410 which is disposed within the inner tube portion 400 and has its forward end disposed in abutment with the plunger 390. The forward end of the elongated member 410 is also configured to engage the forward end of a stressed coil spring 412 which surrounds the central portion of the elongated member within the inner tube portion 400 and has its rearward end engaged with an apertured end wall 414 formed on the rearward end of the inner tube portion 400.

The rearward end of the elongated member 410 is formed with a pair of laterally spaced laterally movable spring fingers 416, the rearward extremities of which are formed with rearwardly and inwardly inclined cam surfaces 418. Extending inwardly from the forward ends of the cam surfaces 418 is a pair of locking shoulders 420 adapted to engage a locking disc 422 seated on the rear centrally apertured wall 414 of the inner tube portion 400. The outer tube 404 includes a rearward end wall 424 formed with cam surfaces 426 which are disposed in engagement with the cam surfaces 418 so as to effect a laterally inward movement of the spring fingers toward one another to disengage locking shoulders 420 from locking ring 422 in response to either a relative rearward movement of the inner tube portion 400 with respect to the outer tube 404 or a relative forward movement of the outer tube 404 with respect to the inner tube portion 400.

The mounting means provided within the plural injecting device 310 to insure actuation of the releasing mechanism 402 as a result of the actuation of the releasing mechanism 348 differs functionally from the mounting means previously described in the devices 10, 110 and 210 in that the mounting means of the plural injecting device 310 is not operable alternatively to actuate the last to be actuated irrespective of which of the plural releasing mechanisms is first to be actuated. To the contrary, the arrangement of the device 310 is that the releasing mechanism 348 is the only one of the two releasing mechanisms provided which is capable of initial actuation. Releasing mechanism 402 can only be actuated as a result of the actuation of releasing mechanism 348. Moreover, the device 310 has individual or plural dosage selectivity, however the only individual dose which can be selected is the dose 334 associated with the releasing mechanism 348.

The plural injecting device 310 includes an outer housing 428 which is formed of two molded halves 430 and 432 rigidly interconnected by a plurality of rivets 434 in a manner similar to that previously provided in connection with the devices 10, 110 and 210. The container support member 320 is slidably mounted within one of the side-by-side cavities provided by the outer housing assembly 428. It will be noted that the forward portions of the outer housing halves 430 and 432 are provided with inwardly turned peripheral flanges 436 through which the nose portion 322 of the member 320 extends. In its normal position, however, the shoulder 324 of the member 320 is spaced rearwardly from the flanges 436, the particular spacing being determined by overriding stop buttons 438 formed on the inner peripheral wall of each of the outer housing halves 430 and 432. The outer tube 370 is mounted within the cavity provided by the outer housing halves against rearward movement by providing inwardly projecting peripheral flanges 440 in the rearward end portions of the housing halves disposed in engagement with the outer tube rear wall 372. A separate safety cap 442 is provided outwardly of the flanges 440, the safety cap including a safety plug 444 which extends within the flanges 440, the central opening in the rear wall 372 of the outer tube 370 and between the spring fingers 360 of the elongated member 356.

It can thus be seen that the initial arrangement is such that when safety cap 442 is removed from its operative position, the associated releasing mechanism 348 can be actuated in a manner similar to that previously described. That is, the user manually grips the outer housing 428 and moves the nose piece 322 into contact with the muscle area to be injected. The relative rearward movement of the first cartridge sub-assembly and elongated member 356 with respect to the outer housing assembly 428 will have the effect of actuating the releasing mechanism 348 so as to cause the spring 346 to move the inner tube 350 rearwardly and simultaneously move the elongated member 356 and first cartridge sub-assembly forwardly. During this latter movement, buttons 438 are easily over-ridden and the tubular support member 320 is moved forwardly until its movement is arrested by engagement with a forked arm 446 of a bell crank lever, generally indicated at 448.

The bell crank lever 448 is pivoted by a pivot pin 450 extended between the outer housing halves 430 and 432 disposed at the forward central portion thereof in a position extending generally laterally of the forked arm 446. The bell crank lever 448 also includes rearwardly extending arm 452 having a locking lug 454 extending laterally from the rearward end thereof. Locking lug 454 normally engages the forward exteriorly flanged end of a tubular actuating member 456 mounted in the rearward portion of the other one of the side-by-side cavities provided by the outer housing assembly 428.

Disposed in surrounding relation with the actuating member 456 is an actuating spring 458, the forward end of which engages the exteriorly flanged forward end of the actuating member 456 and the rearward end of which engages inwardly extending flanges 460 formed on the adjacent rearward portion of the housing halves 430 and 432. The outer tubular member 404 is mounted in axial alignment with the actuating member 456 and extends fowardly therefrom, to a position within a pair of forwardly extending sleeve portions 462 formed integrally on the adjacent forward portions of the housing halves 430 and 432. The forward end of the outer tube 404 as well as the rearward end of the end cap member 384, is slidably mounted within the sleeve portions 462 for movement from the rearwardly disposed normal position shown to a forwardly extended position determined by engagement of the end cap member 384 with an outer nose piece 464. Nose piece 464 is mounted over the sleeve portions 462 for limited forward and rearward movement through the interengagement of peripheral ridges 466 formed on the sleeve portions 462 within an annular groove 468 formed on the interior periphery of the nose piece.

As previously indicated, the releasing mechanism 402 is provided with a separate safety which, as shown, is in the form of a safety plug 470, the forward end of which in its normal operative position engages between the spring fingers 416. The rearward end of the safety plug 470 is formed with an enlargement adapted to snap within the hollow forward end of a stem 472 extending inwardly from a safety cap 474 which engages the exterior surfaces of the flange portions 460.

It will be understood that when the forked arm 466 of bell crank lever 448 is engaged by the shoulder 324 during the forward movement of the member 320 as a result of the actuation of the releasing mechanism 348, lever arm 448 will be pivoted in a clockwise direction as viewed in FIG. 7 about the pivot pin 450. Locking lug 454 on the rearward end of the arm 452 is thus moved laterally outwardly from engagement with the forward end of the actuating member 456. Assuming that safety cap 474 has previously been removed, the resultant release of the stressed actuating spring 458 causes the actuating member 456 to move forwardly which movement is first arrested by engagement of the rearward wall 424 of the outer tube 404. As the outer tube 404 is moved forwardly by the engagement of the actuating member 456, the inner tubular portion 400 and end cap 384 will be moved therewith until such time as the latter engages the nose piece 464 and extends the same to its limiting position, at which time relative movement of the cam surfaces 418 of the spring fingers will take place with respect to the cam surfaces 426 on the outer tube 404 thus moving locking shoulders 420 out of engagement with the locking ring 422 and the effecting of the actuation of the releasing mechanism 402. Stressed spring 412 then acts upon elongated member 410 to move the plunger 390 forward until it engages the rearward enlarged end 398 of the needle 390, thus driving the same outwardly and into the muscle tissue of the user while at the same time the liquid medicament 392 within the container 380 is moved outwardly through the hypodermic needle 394.

In the preceding description, the actuation of the releasing mechanism 402 is described as occurring after the forward movement of the outer tube 404 and inner tube portion 400 together into a forward limiting position before the relative movement necessary to accomplish actuation takes place. It will be understood that such relative movement can occur as a result of the initial movement of the outer tube 404 in which case actuation of the releasing mechanism 402 will occur during the movement of the outer tube 404 toward its limiting position and prior to the inner tube portion 400 reaching its limiting position. In any event, all of the movement takes place with such rapidity that the exact sequence is of no particular consequence.

It will be understood that the limited movement accorded the nose piece 464 enables the user to effect the relative movement of the nose piece 322 with respect to the outer housing 424 required to accomplish the actuation of the releasing member 384. It will be noted that as the nose piece 322 is moved relatively forwardly with respect to the outer housing assembly 428 after actuation of the releasing mechanism 348 (with safety cap 474 removed) the substantially simultaneous actuation of the releasing mechanism 402 or the immediate sequential actuation thereof likewise results in the forward movement of the nose piece 464 as a result of actuation, consequently substantially simultaneous injection takes place with a needle depth within the muscle tissue to the desired extent with respect to both of the hypodermic needles provided.

It will also be noted that when safety cap 474 is retained in its operative position and safety cap 442 is removed it is possible to effect actuation of the releasing mechanism 348 by the actuating procedures heretofore described. Following actuation, as the shoulder 324 of the support member 320 is arrested by engagement with the forked arm 446, bell crank lever 448 will be pivoted so that the locking lug 454 is moved outwardly from the forward end of the actuating member 456. The actuating member 456 then moves forwardly to effect a forward movement of the outer tube 404 and inner tube portion 400 to its forward limiting position. However, no relative movement between the inner and outer tubes will take place because of the engagement of the safety plug 470 between the spring fingers 460 and there will be no injection of the dosage 392.

It thus will be seen that the objects of this invention have been fully and effectively accomplished. It will be realized, however, that the foregoing preferred specific embodiment has been shown and described for the purpose of illustrating the functional and structural principles of this invention and is subject to change without departure from such principles. Therefore, this invention includes all modifications encompassed within the spirit and scope of the following claims.

What is claimed is:

1. A plural hypodermic needle and plural spring actuated injecting device comprising outer housing means adapted to be exteriorly manually engaged by a user, actuating means carried by said outer housing means for movement into an actuating position in response to a manual movement by a user with said outer housing means exteriorly manually engaged as aforesaid, a first cylindrical liquid container within said outer housing means, a first hypodermic needle disposed within said outer housing means in a storage position in operative association with said first container, first plunger means within said outer housing means extending into said first container, first spring means operatively associated with said first plunger means within said outer housing means, first releasable means normally retaining said first spring means in a stressed condition within said outer housing means for actuation in response to the movement of said actuating means into said actuating position to effect release of the stressed condition of said first spring means so that the spring force resulting from said release acts upon said first plunger means to move (1) said first hypodermic needle from said storage position to an extended position into the user and (2) liquid within said first container outwardly through said first hypodermic needle into the user;

a second cylindrical liquid container, a second hypodermic needle operatively associated with said second liquid container, second plunger means operatively associated with said second liquid container, second spring means operatively associated with said second plunger means, second releasable means normally retaining said second spring means in a stressed condition operable upon actuation to effect release of the stressed condition of said second spring means, safety means operable (1) when in a safety position with respect to both said first and second releasable means to prevent actuation thereof as aforesaid and (2) when removed from said safety position in relation to said first releasable means to permit the actuation of said first releasable means as aforesaid and from said safety position in relation to said second releasable means to permit actuation thereof, and means mounting said second container, said second hypodermic needle, said second plunger means, said second spring means and said second releasable means within said outer housing means in operative relation to one another as aforesaid so that when said safety means is removed from said safety position in relation to said second releasable means the latter will be actuated as a result of the actuation of said first releasable means so that the spring force resulting from the release of said second spring means by said second releasable means acts upon said second plunger means to move (1) said second hypodermic needle longitudinally outwardly into an extended position into the user in generally side-by-side relation to said first hypodermic needle and (2) liquid within said second container outwardly through said second hypodermic needle into said user.

2. A device as defined in claim 1 wherein said actuating means includes a first tubular member mounted in said outer housing means with a user engaging portion extending outwardly thereof for movement inwardly into an actuating position, said first liquid container and said first hypodermic needle being mounted together within said first tubular member in said storage position with the hypodermic needle extending forwardly from the forward end of said container and the forward free end of said first hypodermic needle disposed inwardly of the patient engaging portion thereof, said first hypodermic needle and container being movable longitudinally outwardly together by said first plunger means from said storage position into said extended position.

3. A device as defined in claim 2 wherein said first releasable means includes a first tube having a first apertured end wall, a first elongated member having first locking fingers disposed in a locked position of engagement within said first apertured end wall and movable laterally inwardly with respect to one another into a released position with respect to said first apertured end wall, a first outer tube slidably receiving said first inner tube therein for relative rearward longitudinal movement with said first elongated member from a normal inoperative position to an operative position, said first outer tube having a first end wall portion cooperable with said first fingers to deflect the latter laterally inwardly into said released position in response to the relative movement of said first inner tube and said first elongated member into said operative position with respect to said first outer tube, said first spring comprising a first coil spring operatively compressed between said first inner tube and said first elongated member disposed within said first inner tube and in surrounding relation with said first elongated member so that actuation of said first releasable means through movement of said first fingers into said release position and release of said first spring will effect a further relative rearward movement of said first inner tube and a relative forward movement of said first elongated member within said outer housing means.

4. A device as defined in claim 3 wherein said second releasable means includes a second tube having a second apertured end wall, a second elongated member having second locking fingers disposed in a locked position of engagement within said second apertured end wall and movable laterally inwardly with respect to one another into a released position with respect to said second apertured end wall, a second outer tube slidably receiving said second inner tube therein for relative rearward longitudinal movement with said second elongated member from a normal inoperative position to an operative position, said first outer tube having a second end wall portion cooperable with said second fingers to deflect the latter laterally inwardly into said released position in response to the relative movement of said second inner tube and said second elongated member into said operative position with respect to said first outer tube, said second spring comprising a second coil spring operatively compressed between said second inner tube and said second elongated member disposed within said second inner tube and in surrounding relation with said second elongated member so that actuation of said second releasable means through movement of said second fingers into said release position and release of said second spring will effect a further relative rearward movement of said second inner tube and a relative forward movement of said second elongated member within said outer housing means.

5. A device as defined in claim 4 wherein said actuating means includes a second tubular member mounted in said outer housing means with a user engaging portion extending outwardly thereof for movement inwardly into an actuating position, said second liquid container and said second hypodermic needle being mounted together within said second tubular member in said storage position with the hypodermic needle extending forwardly from the forward end of said container and the forward free end of said second hypodermic needle disposed inwardly of the patient engaging portion thereof, said second hypodermic needle and container being movable longitudinally outwardly together by said second plunger means from said storage position into said extended position.

6. A device as defined in claim 5 wherein said mounting means comprises means mounting said second outer tube in longitudinally fixed relation with respect to said outer housing means so that when as a result of the actuation of said first releasable means said outer housing means is engaged by the relative forward movement of said first enlongated member, said first tubular member, said first plunger means, said first liquid container and said first hypodermic needle, the movement thus imparted to said outer housing means will be imparted to said second outer tube, thereby effecting the relative movement of said second inner tube and said second elongated member with respect to said second outer tube due to the inertial tendency of said second inner tube, said second elongated member, said second spring, said second tubular member, said second plunger means, said second liquid container, and said second hypodermic needle, to remain stationary.

7. A device as defined in claim 4 or 5 wherein said mounting means comprises means mounting said first and second outer tubes in longitudinally fixed relation within said outer housing means, and means mechanically interconnecting said second inner tube for longitudinal movement with said first inner tube so that said second inner tube will be moved into its operative position with respect to said second outer tube in response to the further relative rearward movement of said first inner tube immediately following actuation of said first releasable means.

8. A device as defined in claim 4 or 5 wherein said mounting means comprises means mounting said first and second outer tubes for longitudinal movement within said outer housing means, and a pivot lever arm mounted in said outer housing means with one end thereof disposed in longitudinal movement transmitting relation with said first outer tube and the other end thereof disposed in longitudinal movement transmitting relation with said second outer tube so that a relative rearward longitudinal movement imparted to said first outer tube by said first inner tube during the aforesaid further relative rearward movement thereof immediately following actuation of said first releasable means will cause said lever arm to impart a corresponding relatively forward longitudinal movement of said second outer tube into its operative position with respect to said second inner tube.

9. A device as defined in claim 4 wherein said mounting means includes means mounting said first tubular member for inward movement through a rearward stroke into said actuating position and for movement from said actuating position under the action of said first spring through a forward stroke greater than said rearward stroke, a bell crank lever pivotally mounted in said outer housing means having a forked arm disposed in a position to be engaged by said first tubular member during the latter portion of forward stroke thereof, said lever also having a locking arm movable from a normal locking position to a releasing position in response to the engagement of said forked arm by said first tubular member, an actuating member normally retained in an inoperative locked position by said locking arm when in its normal locking position, and spring means for moving said actuating member into motion transmitting relation with said second outer tube to effect the relative movement of said second inner tube and said second elongated member with respect to said second outer tube sufficient to actuate said second releasable means.

10. A plural hypodermic needle and plural spring actuated injecting device comprising
outer housing means adapted to be exteriorly manually engaged by a user,
actuating means carried by said outer housing means for movement into an actuating position in response to a manual movement by a user with said outer housing means exteriorly manually engaged as aforesaid,
a first cylindrical liquid container within said outer housing means,
a first hypodermic needle disposed within said outer housing means in a storage position in operative association with said first container,
first plunger means within said outer housing means extending into said first container,
first spring means operatively associated with said first plunger means within said outer housing means, first releasable means normally retaining said first spring means in a stressed condition within said outer housing means for actuation in response to the movement of said actuating means into said actuating position to effect release of the stressed condition of said first spring means so that the spring force resulting from said release acts upon said first plunger means to move (1) said first hypodermic needle from said storage position to an extended position into the user and (2) liquid within said first container outwardly through said first hypodermic needle into the user;
a second cylindrical liquid container,
a second hypodermic needle operatively associated with said second liquid container,
second plunger means operatively associated with said second liquid container,
second spring means operatively associated with said second plunger means,
second releasable means normally retaining said second spring means in a stressed condition operable upon actuation to effect release of the stressed condition of said second spring means,
safety means operable (1) when in a safety position with respect to both said first and second releasable means to prevent actuation thereof as aforesaid and (2) when removed from said safety position in relation to said first releasable means to permit the actuation of said first releasable means as aforesaid and from said safety position in relation to said second releasable means to permit actuation thereof, and
mechanical motion transmitting means operable to transmit a movement occurring as a result of the actuation of said first releasable means to said second releasable means to insure that the spring force resulting from the release of said second spring means by said second releasable means acts upon said second plunger means to move (1) said second hypodermic needle longitudinally outwardly into an extended position into the user in generally side-by-side relation to said first hypodermic needle and (2) liquid within said second container outwardly through said second hypodermic needle into said user.

11. A plural hypodermic needle and plural spring actuated injecting device comprising
outer housing means adapted to be exteriorly manually engaged by a user,
actuating means carried by said outer housing means for movement into an actuating position in response to a manual movement by a user with said outer housing means exteriorly manually engaged as aforesaid,
a first cylindrical liquid container within said outer housing means,
a first hypodermic needle disposed within said outer housing means in a storage position in operative associated with said first container,
first plunger means within said outer housing means extending into said first container,
first spring means operatively associated with said first plunger means within said outer housing means,
first releasable means normally retaining said first spring means in a stressed condition within said outer housing means for actuation in response to the movement of said actuating means into said actuating position to effect release of the stressed condition of said first spring means so that the spring force resulting from said release acts upon said first plunger means to move (1) said first hypodermic needle from said storage position to an extended position into the user and (2) liquid within said first container outwardly through said first hypodermic needle into the user;

a second cylindrical liquid container, a second hypodermic needle operatively associated with said second liquid container, second plunger means operatively associated with said second liquid container, second spring means operatively associated with said second plunger means, p1 second releasable means normally retaining said second spring means in a stressed condition operable upon actuation to effect release of the stressed condition of said second spring means, safety means operable (1) when in a safety position with respect to both said first and second releasable means to prevent actuation thereof as aforesaid and (2) when removed from said safety position in relation to said first releasable means to permit the actuation of said first releasable means as aforesaid and from said safety position in relation to said second releasable means to permit actuation thereof, spring biased actuating means for actuating said second releasable means and means operable as a result of the actuation of said first releasable means for operating said spring biased actuating means to actuate said second releasable means so that the spring force resulting from the release of said second spring means by said second releasable means acts upon said second plunger means to move (1) said second hypodermic needle longitudinally outwardly into an extended position into the user in generally side-by-side relation to said first hypodermic needle and (2) liquid within said second container outwardly through said second hypodermic needle into said user.

* * * * *